US012480157B2

(12) United States Patent
Wu et al.

(10) Patent No.: US 12,480,157 B2
(45) Date of Patent: Nov. 25, 2025

(54) POLYNUCLEOTIDE SEQUENCING

(71) Applicant: ILLUMINA, INC., San Diego, CA (US)

(72) Inventors: Xiaolin Wu, Cambridge (GB); Patrick McCauley, Cambridge (GB)

(73) Assignee: Illumina, Inc., San Diego, CA (US)

( * ) Notice: Subject to any disclaimer, the term of this patent is extended or adjusted under 35 U.S.C. 154(b) by 625 days.

(21) Appl. No.: 17/952,414

(22) Filed: Sep. 26, 2022

(65) Prior Publication Data

US 2023/0096386 A1 Mar. 30, 2023

Related U.S. Application Data

(60) Provisional application No. 63/250,516, filed on Sep. 30, 2021.

(51) Int. Cl.

| | |
|---|---|
| ***C12Q 1/6874*** | (2018.01) |
| ***B01L 3/00*** | (2006.01) |
| ***C12Q 1/6806*** | (2018.01) |

(52) U.S. Cl.

CPC ...... *C12Q 1/6874* (2013.01); *B01L 3/502761* (2013.01); *B01L 2200/04* (2013.01); *B01L 2200/0647* (2013.01); *B01L 2200/16* (2013.01); *C12Q 1/6806* (2013.01)

(58) Field of Classification Search

CPC .. C12Q 1/6874; C12Q 1/6806; C12Q 1/6848; B01L 3/502761; B01L 2200/04; B01L 2200/0647; B01L 2200/16

See application file for complete search history.

(56) References Cited

U.S. PATENT DOCUMENTS

| | | | |
|---|---|---|---|
| 2013/0137091 | A1 | 5/2013 | Gordon et al. |
| 2018/0044715 | A1 | 2/2018 | Iyidogan et al. |
| 2020/0190576 | A1 | 6/2020 | Gatti-Lafranconi et al. |

FOREIGN PATENT DOCUMENTS

| | | | |
|---|---|---|---|
| CA | 3103744 | * 6/2020 | ........... C12Q 1/6869 |

OTHER PUBLICATIONS

International Patent Application No. PCT/EP2022/076989, filed Sep. 28, 2022; International Search Report issued Jan. 20, 2023.

* cited by examiner

*Primary Examiner* — Cynthia B Wilder

(74) *Attorney, Agent, or Firm* — Mueting Raasch Group

(57) ABSTRACT

A polynucleotide sequencing method includes a wash step that employs a composition including a polymerase. The composition may also include a plurality of nucleotides. The composition may be configured to prevent the polymerase from incorporating one of the plurality of nucleotides into a copy polynucleotide strand. The composition may be substantially free of $Mg^{2+}$.

12 Claims, 7 Drawing Sheets

POLYNUCLEOTIDE SEQUENCING

CROSS REFERENCE TO RELATED APPLICATIONS

This application claims the benefit of U.S. Provisional Patent Application No. 63/250,516, filed on Sep. 30, 2021, which provisional application is hereby incorporated by reference in its entirety.

FIELD

The present disclosure relates to, among other things, sequencing of polynucleotides.

INTRODUCTION

Sequencing of a template polynucleotide strand may occur through multiple cycles of steps by which one detectable nucleotide per cycle is incorporated into a copy strand complementary to the template strand. The detectable nucleotides are typically blocked to prevent incorporation of more than one detectable nucleotide per cycle. After an incubation time, a wash step is typically performed to remove any unincorporated detectable nucleotide. A detection step, in which the identity of the detectable nucleotide incorporated into the copy strand is determined, may then performed. Next, an unblocking step and cleavage or masking step is performed in which the blocking agent is removed from the last incorporated nucleotide in the copy strand, and the detectable moiety is cleaved from or masked on the last nucleotide incorporated into the copy strand. In some instances, the step of removing the blocking moiety also removes the detectable moiety. The cycle is then repeated by introducing blocked, detectable nucleotides in an incorporation step.

Various compositions are employed at each step of a cycle of sequencing. For example, an incorporation composition comprising a polymerase and nucleotides are employed during the incorporation step. A scan composition that may include, among other things, an antioxidant to protect the polynucleotides from photo-induced damage during the detection step when, for example, the nucleotides include fluorophore labels for detection. A de-blocking composition that includes reagents for cleaving the blocking moiety from the nucleotide incorporated is employed during the de-blocking step. A post-cleave wash composition that may include a scavenger compound to protect the polynucleotides, enzymes or other sequencing reagents from reactive compounds used in, or resulting from, the de-blocking step may be used following the de-blocking step.

A great deal of trial and error and consideration is typically employed to develop the compositions and reagents used at each step of sequencing to reduce errors in sequencing, to increase the rate of sequencing, to increase the number of sequencing cycles that may be performed until the identity of the previously incorporated nucleotide can no longer be reliably determined, and the like. Despite the care taken in developing sequencing reagents and compositions, some issues remain. For example, a substantial amount of residual signal from the previously incorporated nucleotide remains after a de-blocking step. The residual signal may increase noise, which may interfere with the ability to accurately identify the nucleotide incorporated in the next sequencing cycle.

SUMMARY

The present disclosure describes, among other things, polynucleotide sequencing methods that employ a wash composition that includes a polymerase. Surprisingly, it has been found that employing a polymerase in a wash composition reduces residual signal following a de-block step. Even more surprisingly, the incorporation of the polymerase in the wash composition may improve other sequencing metrics, such as reducing one or more of phasing, pre-phasing, error rate, and signal decay. The use of a polymerase in a wash composition may also permit shorter sequencing cycle time. For example, the use of a polymerase in a wash composition may permit reduction in duration of an incorporation step.

While the mechanism regarding how the wash composition comprising the polymerase reduces residual signal is not completely understood, it is possible that the polymerase in the wash composition (a "second" polymerase) facilitates removal of the sequencing polymerase (a "first" polymerase) from the copy strand or the template strand. The first polymerase may accept or retain a cleaved detectable moiety. Accordingly, removal of the bound first polymerase may result in reduction of the residual signal. If the wash composition comprising the second polymerase facilitates removal of the bound first polymerase, use of the wash composition before or after the deblocking step may reduce the residual signal.

The mechanism or mechanisms regarding how the wash composition comprising the polymerase may reduce phasing and pre-phasing and may affect other sequencing metrics is or are also not well understood. Regardless of the mechanism or mechanisms involved, the use of a wash composition comprising a polymerase may surprisingly provide benefits to sequencing.

In some embodiments described herein, a polynucleotide sequencing method comprises (a) incubating an incorporation composition comprising a first polymerase and a plurality of blocked, labeled nucleotides with a template polynucleotide strand such that the polymerase incorporates one of the plurality of blocked, labeled nucleotides into a copy polynucleotide strand complementary to at least a portion of the template polynucleotide strand; (b) identifying the blocked, labeled nucleotide incorporated into the copy polynucleotide strand; (c) removing a label and a blocking moiety from the blocked, labeled nucleotide incorporated into the copy polynucleotide strand; (d) washing the removed label and the blocking moiety away from the copy polynucleotide strand with a first wash composition comprising a second polymerase; and (e) repeating steps (a) to (d) until at least a partial sequence of the template polynucleotide strand is determined.

In some embodiments described herein, a polynucleotide sequencing method comprises (a) incubating an incorporation composition comprising a first polymerase and a plurality of blocked, labeled nucleotides with a template polynucleotide strand such that the polymerase incorporates one of the plurality of blocked, labeled nucleotides into a copy polynucleotide strand complementary to at least a portion of the template polynucleotide strand; (b) identifying the blocked, labeled nucleotide incorporated into the copy polynucleotide strand; (c) contacting the copy polynucleotide strand into which the blocked, labeled nucleotide is incorporated with a first wash composition comprising a second polymerase; (d) removing a label and a blocking moiety from the blocked, labeled nucleotide incorporated into the copy polynucleotide strand; (e) washing the removed label and the blocking moiety away from the copy polynucleotide strand with a second wash composition; and (f) repeating steps (a) to (e) until at least a partial sequence of the template polynucleotide strand is determined.

The first polymerase and the second polymerase may be the same polymerase or may be a different polymerase.

The first wash composition may comprise a plurality of nucleotides. The nucleotides may comprise blocking moieties. The nucleotides may comprise detectable moieties. The first wash composition may be configured to prevent the second polymerase from incorporating a nucleotide into the copy polynucleotide strand. For example, the first wash composition may be substantially free of magnesium ion ($Mg^{2+}$). The first wash composition may be substantially the same as the incorporation composition, except that the first wash composition is substantially free of $Mg^{2+}$.

In some embodiments described herein, a cartridge for use with a sequencing apparatus comprises (a) a first chamber comprising an incorporation composition comprising a first plurality of reagents for incorporating a blocked, labeled nucleotide into a copy polynucleotide strand complementary to at least a portion of a template polynucleotide strand; (b) a second chamber comprising a detection composition for identifying the blocked, labeled nucleotide incorporated into the copy polynucleotide strand; (c) a third chamber comprising a cleavage composition comprising a second plurality of reagents for removing a label and a blocking moiety from the blocked, labeled nucleotide incorporated into the copy polynucleotide strand; and (d) a fourth chamber comprising a first wash composition comprising a polymerase and a plurality of nucleotides, wherein the first wash composition is configured to prevent the second polymerase from incorporating one of the plurality of nucleotides into the copy polynucleotide strand.

The first polymerase and the second polymerase may be the same polymerase or may be a different polymerase.

The first wash composition may comprise a plurality of nucleotides. The nucleotides may comprise blocking moieties. The nucleotides may comprise detectable moieties. The first wash composition may be configured to prevent the second polymerase from incorporating a nucleotide into the copy polynucleotide strand. For example, the first wash composition may be substantially free of magnesium ion ($Mg^{2+}$). The first wash composition may be substantially the same as the incorporation composition, except that the first wash composition is substantially free of $Mg^{2+}$.

The cartridge may comprise a fifth chamber comprising a second wash composition. The second wash composition may be substantially free of a polymerase and nucleotides.

In some embodiments described herein, a kit for use with a sequencing apparatus comprises (a) a first container containing an incorporation composition comprising a first plurality of reagents for incorporating a blocked, labeled nucleotide into a copy polynucleotide strand complementary to at least a portion of a template polynucleotide strand; (b) a second container comprising a detection composition for identifying the blocked, labeled nucleotide incorporated into the copy polynucleotide strand; (c) a third container comprising a cleavage composition comprising a second plurality of reagents for removing a label and a blocking moiety from the blocked, labeled nucleotide incorporated into the copy polynucleotide strand; and (d) a fourth container comprising a first wash composition comprising a polymerase and a plurality of nucleotides, wherein the first wash composition is configured to prevent the second polymerase from incorporating one of the plurality of nucleotides into the copy polynucleotide strand.

The first wash composition may comprise a plurality of nucleotides. The nucleotides may comprise blocking moieties. The nucleotides may comprise detectable moieties. The first wash composition may be configured to prevent the second polymerase from incorporating a nucleotide into the copy polynucleotide strand. For example, the first wash composition may be substantially free of magnesium ion ($Mg^{2+}$). The first wash composition may be substantially the same as the incorporation composition, except that the first wash composition is substantially free of $Mg^{2+}$.

The kit may comprise a fifth container comprising a second wash composition. The second wash composition may be substantially free of a polymerase and nucleotides.

The kit may comprise instructions for using said kit.

The details of one or more embodiments are set forth in the accompanying drawings and the description below. Other features, objects, and advantages will be apparent from the description and drawings, and from the claims.

It is to be understood that both the foregoing general description and the following detailed description present embodiments of the subject matter of the present disclosure and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

DESCRIPTION OF DRAWINGS

The following detailed description of specific embodiments of the present disclosure may be best understood when read in conjunction with the following drawings.

Figure 1:
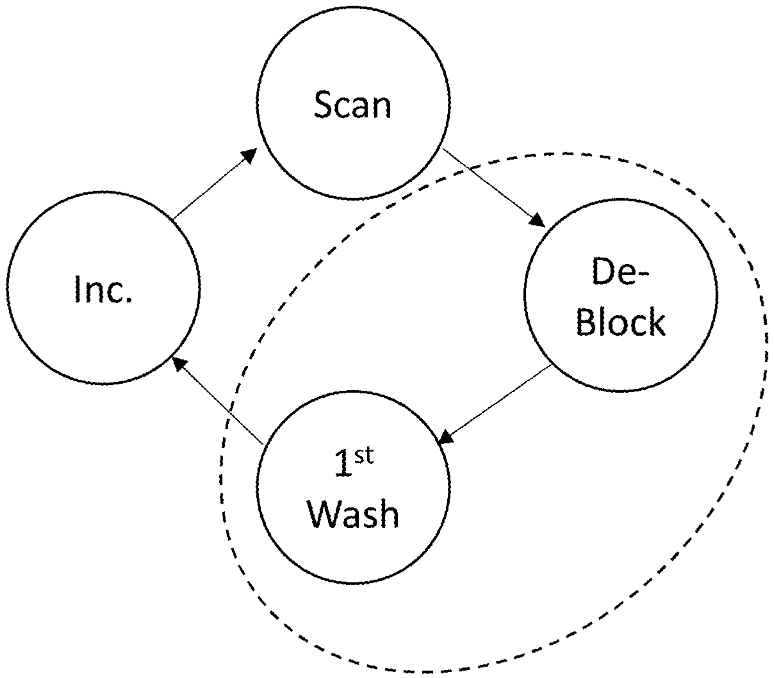
FIGS. 1-3 are schematic diagrams of some steps of sequencing processes illustrating some compositions employed at the various steps.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms “a,” “an” and “the” include plural referents unless the context clearly dictates otherwise. Thus, for example, reference to a “template polynucleotide sequence” includes examples having two or more such “template polynucleotide sequences” unless the context clearly indicates otherwise.

As used in this specification and the appended claims, the term “or” is generally employed in its sense including “and/or” unless the content clearly dictates otherwise. The term “and/or” means one or all of the listed elements or a combination of any two or more of the listed elements. The use of “and/or” in some instances does not imply that the use of “or” in other instances may not mean “and/or.”

As used herein, “have”, “has”, “having”, “include”, “includes”, “including”, “comprise”, “comprises”, “comprising” or the like are used in their open-ended inclusive sense, and generally mean “include, but not limited to”, “includes, but not limited to”, or “including, but not limited to”.

“Optional” or “optionally” means that the subsequently described event, circumstance, or component, can or cannot occur, and that the description includes instances where the event, circumstance, or component, occurs and instances where it does not.

The words “preferred” and “preferably” refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

In addition, the recitations herein of numerical ranges by endpoints include all numbers subsumed within that range (e.g., 1 to 5 includes 1, 1.5, 2, 2.75, 3, 3.80, 4, 5, etc.). Where a range of values is “greater than”, “less than”, etc. a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. However, it will be understood that a presented order is one embodiment of an order by which the method may carried out. Any recited single or multiple feature or aspect in any one claim may be combined or permuted with any other recited feature or aspect in any other claim or claims.

While various features, elements or steps of particular embodiments may be disclosed using the transitional phrase “comprising,” it is to be understood that alternative embodiments, including those that may be described using the transitional phrases “consisting of” or “consisting essentially of,” are implied. Thus, for example, implied alternative embodiments to a method comprising an incorporation step, a detection step, a deprotection step, and one or more wash steps includes embodiments where the method consists of enumerated steps and embodiments where the method consists essentially of the enumerated. The phrase “consisting essentially of” means a recited list of one or more items belonging to an article, kit, system, method, or the like and other non-listed items that do not materially affect the basic and novel characteristics or properties of the article, kit, system, method, or the like.

The terms “first,” “second,” “third,” and so forth as used herein are used as labels for nouns that they precede, and do not imply any type of ordering (e.g., spatial, temporal, logical, numerical, etc.) unless such an ordering is otherwise explicitly indicated. For example, a “second” feature does not require that a “first” feature be present or does not require that a “first” feature be implemented prior to the “second” feature, unless otherwise specified.

Various components may be described as “configured to” perform a task or tasks. In such contexts, “configured to” is a broad recitation generally meaning “having structure that” performs the task or tasks during operation. As such, the component can be configured to perform the task even when the component is not currently performing that task (e.g., a wash composition configured to prevent a polymerase from incorporating a nucleotide in a copy strand may comprise a component that prevents the polymerase from incorporating a nucleotide or may lack a component needed for the polymerase to incorporate the nucleotide).

As used herein, “providing” in the context of a compound, composition, kit, article, system, or the like means making the compound, composition, kit, article, system, or the like, purchasing the compound, composition, kit, article, system, or the like, or otherwise obtaining the compound, composition, kit, article, system, or the like.

Concentrations of molecules in compositions are expressed herein in terms of percent by weight unless otherwise indicated.

As used herein, the term “polymerase” is an enzyme that produces a copy replicate of a polynucleotide using the polynucleotide as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases may use a short RNA or DNA strand, called a primer, to begin strand growth. Some polymerases may displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" and its derivatives refer generally to any polynucleotide that may hybridize to a target sequence of interest. Typically, the primer functions as a substrate onto which nucleotides may be polymerized by a polymerase; in some embodiments, however, the primer may become incorporated into the synthesized polynucleotide strand and provide a site to which another primer may hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide.

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). As used herein, "amplified target sequences" and its derivatives, refers generally to a polynucleotide sequence produced by the amplifying the target sequences using target-specific primers and the methods provided herein. The amplified target sequences may be either of the same sense (i.e the positive strand) or antisense (i.e., the negative strand) with respect to the target sequences.

Suitable nucleotides for use in the provided methods include, but are not limited to, deoxynucleotide triphosphates, deoxyadenosine triphosphate (dATP), deoxythymidine triphosphate (dTTP), deoxycytidine triphosphate (dCTP), and deoxyguanosine triphosphate (dGTP). Optionally, the nucleotides used in the provided methods, whether labeled or unlabeled, can include a blocking moiety such as a reversible terminator moiety that inhibits chain extension. Suitable labels for use on the labeled nucleotides include, but are not limited to, haptens, radionucleotides, enzymes, fluorescent labels, chemiluminescent labels, and chromogenic agents.

A polynucleotide will generally contain phosphodiester bonds, although in some cases nucleic acid analogs can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Polynucleotides containing one or more carbocyclic sugars are also included within the definition of polynucleotides (see Jenkins et al., Chem. Soc. Rev. (1995) pp 169-176). Several polynucleotide analogs are described in Rawls, C & E News Jun. 2, 1997 page 35. All these references are hereby expressly incorporated by reference. These modifications of the ribose-phosphate backbone may be done to facilitate the addition of labels, or to increase the stability and half-life of such molecules in physiological environments.

A polynucleotide will generally contain a specific sequence of four nucleotide bases: adenine (A); cytosine (C); guanine (G); and thymine (T). Uracil (U) can also be present, for example, as a natural replacement for thymine when the nucleic acid is RNA. Uracil can also be used in DNA. A polynucleotide may also include native or non-native bases. In this regard, a native deoxyribonucleic acid polynucleotide may have one or more bases selected from the group consisting of adenine, thymine, cytosine or guanine and a ribonucleic acid may have one or more bases selected from the group consisting of uracil, adenine, cytosine or guanine. It will be understood that a deoxyribonucleic acid polynucleotide used in the methods or compositions set forth herein may include, for example, uracil bases and a ribonucleic acid can include, for example, a thymine base. Exemplary non-native bases that may be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. Optionally, isocytosine and isoguanine may be included in a nucleic acid in order to reduce non-specific hybridization, as generally described in U.S. Pat. No. 5,681,702, which is incorporated by reference herein in its entirety.

A non-native base used in a polynucleotide may have universal base pairing activity such that it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which base pairs with cytosine, adenine or uracil.

Incorporation of a nucleotide into a polynucleotide strand refers to joining of the nucleotide to a free 3' hydroxyl group of the polynucleotide strand via formation of a phosphodiester linkage with the 5' phosphate group of the nucleotide. The polynucleotide template to be sequenced can be DNA or RNA, or even a hybrid molecule that includes both deoxynucleotides and ribonucleotides. The polynucleotide can include naturally occurring and/or non-naturally occurring nucleotides and natural or non-natural backbone linkages.

Phasing and pre-phasing are terms known to those of skill in the art and are used to describe the loss of synchrony in the readout of the sequence copies of a cluster. Phasing and pre-phasing cause the extracted intensities for a specific cycle to consist of the signal of the current cycle as well as noise from the preceding and following cycles. Thus, as used herein, the term “phasing” refers to a phenomenon in sequencing by synthesis (SBS) that is caused by incomplete incorporation of a nucleotide in some portion of polynucleotide strands within clusters by polymerases at a given sequencing cycle, and is thus a measure of the rate at which single molecules within a cluster loose sync with each other. Phasing can be measured during detection of cluster signal at each cycle, and can be reported as a percentage of detectable signal from a cluster that is out of synchrony with the signal in the cluster. As an example, a cluster is detected by a “green” fluorophore signal during cycle N. In the subsequent cycle (cycle N+1), 99.9% of the cluster signal is detected in the “red” channel and 0.1% of the signal remains from the previous cycle and is detected in the “green” channel. This result would indicate that phasing is occurring, and can be reported as a numerical value, such as a phasing value of 0.1, indicating that 0.1% of the molecules in the cluster are falling behind at each cycle.

The term “pre-phasing” as used herein refers to a phenomenon in SBS that is caused by the incorporation of nucleotides without effective 3' terminators, causing the incorporation event to go 1 cycle ahead. As the number of cycles increases, the fraction of sequences per cluster affected by phasing increases, hampering the identification of the correct base. Pre-phasing can be detected by a sequencing instrument and reported as a numerical value, such as a pre-phasing value of 0.1, indicating that 0.1% of the molecules in the cluster are running ahead at each cycle.

Detection of phasing and pre-phasing can be performed and reported according to any suitable methodology as is known in the art, for example, as described in U.S. 2012/0020537, which is incorporated by reference in its entirety.

The present disclosure describes, among other things, polynucleotide sequencing methods and compositions, kits, equipment, and equipment components or accessories for use in the sequencing methods. The methods and compositions, kits, equipment, components, or accessories may allow for longer sequencing runs, meaning that more sequencing cycles may be performed until the identity of the previously incorporated nucleotide can no longer be reliably determined. The methods and compositions, kits, equipment, components, or accessories may reduce error rates. Errors may occur when, among other things, when an incorrect nucleotide is incorporated into the copy strand, or when phasing occurs.

As discussed throughout, provided are improved methods for sequencing polynucleotides. Exemplary sequencing methods are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. One useful method for high throughput or rapid sequencing is sequencing by synthesis (SBS). SBS techniques include, but are not limited to, the Genome Analyzer systems (Illumina Inc., San Diego, CA) and the True Single Molecule Sequencing (tSMS)™ systems (Helicos BioSciences Corporation, Cambridge, MA). Briefly, a number of sequencing by synthesis reactions are used to elucidate the identity of a plurality of bases at target positions within a target sequence. All these reactions rely on the use of a target nucleic acid sequence (template polynucleotide) having at least two domains; a first domain to which a sequencing primer will hybridize, and an adjacent second domain, for which sequence information is desired. Upon formation of an assay complex, extension enzymes, such as polymerases, are used to add deoxynucleotide triphosphates (dNTPs) to a sequencing primer that is hybridized to first domain, and each addition of dNTPs is read to determine the identity of the added dNTP. This may proceed for many cycles. SBS techniques such as, the Genome Analyzer systems (Illumina Inc., San Diego, CA) and the True Single Molecule Sequencing (tSMS)™ systems (Helicos BioSciences Corporation, Cambridge, MA), utilize labeled nucleotides to determine the sequence of a target nucleic acid molecule. A target nucleic acid molecule (template polynucleotide) can be hybridized with a primer and incubated in the presence of a polymerase and a labeled nucleotide containing a blocking group. The primer is extended such that the nucleotide is incorporated. The presence of the blocking group permits only one round of incorporation, that is, the incorporation of a single nucleotide. The presence of the label permits identification of the incorporated nucleotide. A plurality of homogenous single nucleotide bases can be added during each cycle, such as used in the True Single Molecule Sequencing (tSMS)™ systems (Helicos BioSciences Corporation, Cambridge, MA) or, alternatively, all four nucleotide bases can be added during each cycle simultaneously, such as used in the Genome Analyzer systems (Illumina Inc., San Diego, CA), particularly when each base is associated with a distinguishable label. After identifying the incorporated nucleotide by its corresponding label, both the label and the blocking group can be removed, thereby allowing a subsequent round of incorporation and identification. Determining the identity of the added nucleotide base includes, in some embodiments, repeated exposure of the newly added labeled bases a light source that can induce a detectable emission due the addition of a specific nucleotide base, i.e. dATP, dCTP, dGTP or dTTP. The methods and compositions disclosed herein are particularly useful for such SBS techniques. In addition, the methods and compositions described herein may be particularly useful for sequencing from an array of nucleic acids, where multiple sequences can be read simultaneously from multiple positions on the array since each nucleotide at each position can be identified based on its identifiable label. Exemplary methods are described in US 2009/0088327; US 2010/0028885; and US 2009/0325172, each of which is incorporated herein by reference.

The polynucleotide sequence methods described herein include an incorporation step in which a blocked labeled nucleotide is incorporated into a copy polynucleotide strand based on a sequence of a template strand. During the incorporation step an incorporation composition comprising a first polymerase and a plurality of blocked, labeled nucleotides is incubated with a template polynucleotide strand such that the first polymerase incorporates one of the plurality of blocked, labeled nucleotides into a copy polynucleotide strand complementary to at least a portion of the template polynucleotide strand.

The polynucleotide sequencing methods also include an identification step in which the identify of the blocked, labeled nucleotide incorporated into the copy polynucleotide strand is determined. The methods further include a de-blocking step in which a label and a blocking moiety are removed from the blocked, labeled nucleotide incorporated into the copy polynucleotide strand. The polynucleotide sequencing methods include at least a first wash step, and may optionally comprise one or more additional wash steps, in which reagents or components from a previous step are washed away from the template strand and the copy strand before introducing a composition comprising reagents or components for the next step. The template strand, the copy strand, or the template strand and the copy strand are preferably immobilized on a solid support so that the template strand and the copy strand are not washed away during a wash step.

In the first wash step, the copy strand, and thus the hybridized template strand, are incubated with a first wash composition. The first wash composition includes a second polymerase. Wash compositions for sequencing methods have not previously included a polymerase because polymerases are generally expensive relative to other components of the wash compositions and because polymerases would not have been thought to provide a benefit for inclusion in a wash composition. However, as described herein, the inclusion of the second polymerase in the first wash composition may reduce residual signal following a de-block step. Incorporation of the second polymerase in the first wash composition may improve other sequencing metrics, such as reducing one or more of phasing, pre-phasing, error rate, and signal decay. Incorporation of the second polymerase in the first wash composition may permit reduced sequence cycle time without substantially impacting sequencing accuracy. For example, the duration of the incorporation step may be reduced.

Without intending to be bound by theory, it is believed that the first (sequencing) polymerase retains or accepts a detectable moiety cleaved during a de-blocking step and that the first wash composition comprising the second polymerase facilitates displacement of the first polymerase. If the first wash composition comprising the second polymerase facilitates removal of the bound first polymerase, use of the first wash composition before or after the deblocking step may reduce the residual signal.

The first polymerase may be damaged by a reactive oxygen species induced by an identification step that employs a light source capable of generating the reactive oxygen species. Such damage may result in the first polymerase remaining bound to the template strand and/or the copy strand during the scan step. The damaged bound first polymerase may retain or accept a detectable moiety cleaved during a de-blocking step. The first wash step may facilitate displacement of the damaged first bound polymerase.

In some embodiments, the first wash composition is introduced after a de-blocking step in a sequencing cycle. For example, the first wash composition may be introduced after a de-blocking step and before an incorporation step.

In some embodiments, the first wash composition is introduced before a de-blocking step in a sequencing cycle. For example, the first wash composition may be introduced after an identification step and before a de-blocking step.

The first wash composition may be introduced after an incorporation step and before an identification step and before a de-blocking step.

The first wash composition may comprise any suitable polymerase. In some embodiments, the second polymerase in the first wash composition is the same as the first polymerase used in the incorporation step. The second polymerase may be different from the first polymerase. The first polymerase may be developed to rapidly and accurately incorporate blocked, labeled nucleotides into the copy strand based on the sequence of the template strand under sequencing conditions. The second polymerase may not need to be so refined.

In some embodiments, the first polymerase is a DNA polymerase. In some embodiments, the second polymerase is a DNA polymerase.

The second polymerase may be present in the first wash composition at any suitable concentration. For example, the second polymerase may be present in the first wash composition at a concentration from 10 micrograms per milliliter to 150 micrograms per milliliter, such as from 20 micrograms per milliliter to 120 micrograms per milliliter, or from 30 micrograms per milliliter to 100 micrograms per milliliter. In some embodiments, the second polymerase is present in the first wash composition at a concentration that is within 50% of the concentration of the first polymerase in the incorporation composition. For example, the second polymerase is present in the first wash composition at a concentration that is within 40% of the concentration of the first polymerase in the incorporation composition, within 30% of the concentration of the first polymerase in the incorporation composition, within 20% of the concentration of the first polymerase in the incorporation composition, or within 10% of the concentration of the first polymerase in the incorporation composition.

The first wash composition may comprise a plurality of nucleotides. For example, the plurality of nucleotides may comprise nucleotides sufficient to permit a polymerase to incorporate one of the plurality of nucleotides into a copy strand regardless of the sequence of the template strand. For example, the plurality of nucleotides may comprise dATP, dTTP, dCTP, dGTP or labeled derivatives thereof, blocked derivatives thereof, or labeled and blocked derivatives thereof. In some embodiments, the plurality of nucleotides in the first wash composition are not blocked or labeled. In some embodiments, the plurality of nucleotides in the first wash composition are blocked. In some embodiments, the plurality of nucleotides in the first wash composition are labeled. In some embodiments, the plurality of nucleotides in the first wash composition are blocked and labeled. In some embodiments, the plurality of nucleotides in the first wash composition are the same as the plurality of nucleotides in the incorporation composition. In some embodiments, the plurality of nucleotides in the first wash composition are different than the plurality of nucleotides in the incorporation composition.

The plurality of nucleotides may be present in the first wash composition at any suitable concentration. For example, any one of the plurality of nucleotides may be present in the first wash composition at a concentration from 0.5 micromolar to 15 micromolar, such as from 0.5 micromolar to 10 micromolar, or from 1 micromolar to 5 micromolar. Preferably, each of the plurality of nucleotides is present in the first wash composition at a concentration that is substantially the same (e.g., within 10%) as each of the other of the plurality of nucleotides in the first wash composition.

In some embodiments, the each of the plurality of nucleotides is present in the first wash composition at a concentration that is within 50% of the concentration of each of the plurality of nucleotides in the incorporation composition. For example, the second polymerase is present in the first wash composition at a concentration that is within 40% of the concentration of the first polymerase in the incorporation composition, within 30% of the concentration of the first polymerase in the incorporation composition, within 20% of the concentration of the first polymerase in the incorporation composition, or within 10% of the concentration of the first polymerase in the incorporation composition.

Preferably, the first wash composition is configured to prevent the second polymerase from incorporating one of the plurality of nucleotides into the copy polynucleotide strand. The first wash composition may comprise a polymerase inhibitor. The second polymerase may be modified such that the ability of the second polymerase activity to incorporate a nucleotide into the copy strand is inhibited or prevented. The first wash composition may lack or substantially lack a component required for polymerase activity. In some embodiments, the first wash composition is substantially free of $Mg^{2+}$. As used herein, "substantially free of $Mg^{2+}$" means that the first was composition comprises a sufficiently low concentration of $Mg^{2+}$ to inhibit or prevent the second polymerase from incorporating a nucleotide into the copy strand. Preferably, the first wash composition is free of $Mg^{2+}$. The first wash composition may comprise a de minimis amount of $Mg^{2+}$.

The first wash composition may comprise components of a scan composition. Accordingly, the first wash composition may be used as the scan composition during the identification step. The first wash composition may comprise an antioxidant to protect the template strand and the copy strand from damage that may be induced by light during the identification step. or other suitable scan composition components. The first wash composition may comprise any suitable amount of an antioxidant. For example, the first wash composition may comprise one or more antioxidant in a combined total antioxidant concentration from about 2 mM to about 50 mM, such as from about 5 mM to about 40 mM, or from about 15 mM to about 25 mM, or about 20 mM. Suitable antioxidants include ascorbate, acetovanillone, and 6-hydroxy-2,5,7,8-tetramethylchroman-2-carboxylic acid (Trolox). In some preferred embodiments, the first wash composition comprises sodium ascorbate.

The first wash composition may comprise components of a de-block composition. Accordingly, the first wash composition may be used as the de-block composition during the de-blocking step. The first wash composition may comprise a cleavage agent configured to cleave or remove a blocking moiety and/or a labeled moiety from a blocked, labeled nucleotide. Preferably, cleavage agent removes both the blocking moiety and the labeled moiety. Additional components of a de-block composition that may be included in the first wash composition, as well as additional details regarding the cleavage agent, are discussed below regarding the de-block composition.

The first wash composition may include any other suitable components. Preferably, the first wash composition comprises a buffer compatible with subsequent step of the sequencing procedure; e.g., incorporation of the next blocked, labeled nucleotide in the sequence if used prior to an incorporate step.

The first wash composition may comprise a buffer, such as Tris buffer. The buffer may be present at any suitable concentration. For example, the buffer may be present at a concentration from about 5 mM to about 2 M such as from about 10 mm to about 1.5 M, or from about 50 mM to about 1M. In some preferred embodiments, the first wash composition comprises a Tris buffer at a concentration from about 75 mM to about 250 mM, such from about 100 mM to about 200 mM, or about 150 mM.

The first wash composition may comprise a detergent. Any suitable detergent may be included in the first wash composition. For example, the first wash composition may comprise an anionic, cationic, zwitterionic or nonionic detergent. In some preferred embodiments, the first wash composition comprises a nonionic detergent. An example of a suitable nonionic detergent is Tween 20 (available from ThermoFischer Scientific). The detergent may be present in the first wash composition at any suitable concentration. For example, the detergent may be present in the first wash composition from about 0.01% by weight to about 0.5% by weight, such as from about 0.02% by weight to about 0.1% by weight, or from about 0.03% by weight to about 0.07% by weight. In some preferred embodiments, the first wash composition comprises Tween 20 at a concentration from about 0.03% by weight to about 0.07% by weight, or about 0.5% by weight.

The first wash composition may comprise a chelating agent. Any suitable chelating agent may be included in the first wash composition. For example, the first wash composition may comprise dihydroxyethylglycine (HEG) or ethylenediaminetetraacetic acid (EDTA). The chelating agent may be present in any suitable concentration. For example, the chelating agent may be present in the first wash composition at a concentration from about 0.1 mM to about 50 mM, such as from about 0.5 mM to about 20 mM. In some preferred embodiments, the first wash composition comprises HEG at a concentration from about 5 mM to about 15 mM, such as about 10 mM.

The first wash composition may comprise a salt. For example, the first wash composition may comprise sodium chloride. The salt may be present in the first wash composition at any suitable concentration. For example, the salt may be present at a concentration from about 10 mM to about 250 mM, such as from about 25 mM to about 100 mM, from about 30 mM to about 70 mM, or about 50 mM.

Figure 2:
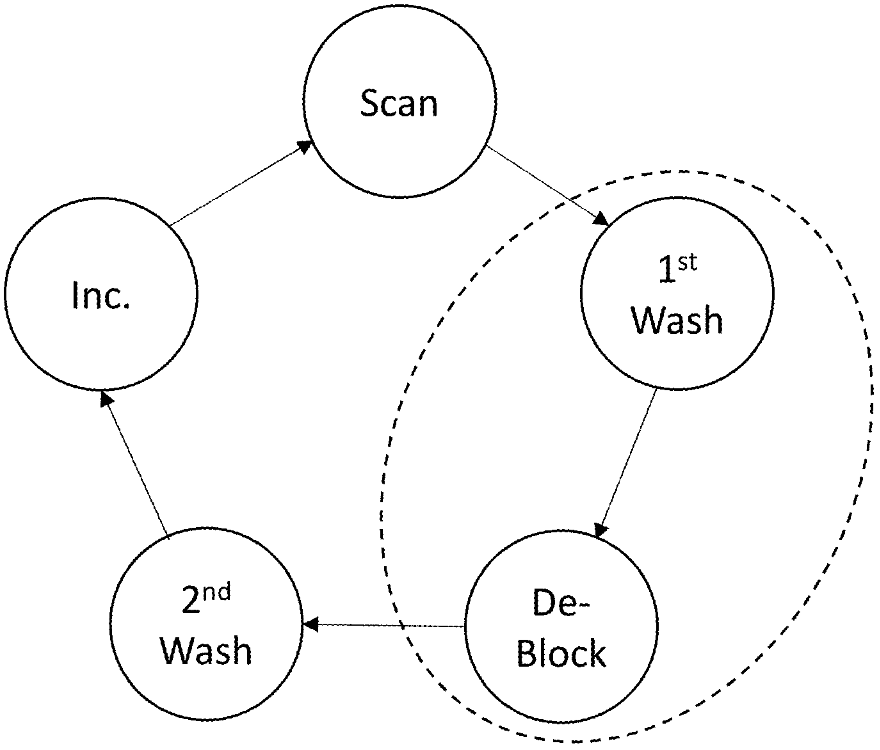
Figure 3:
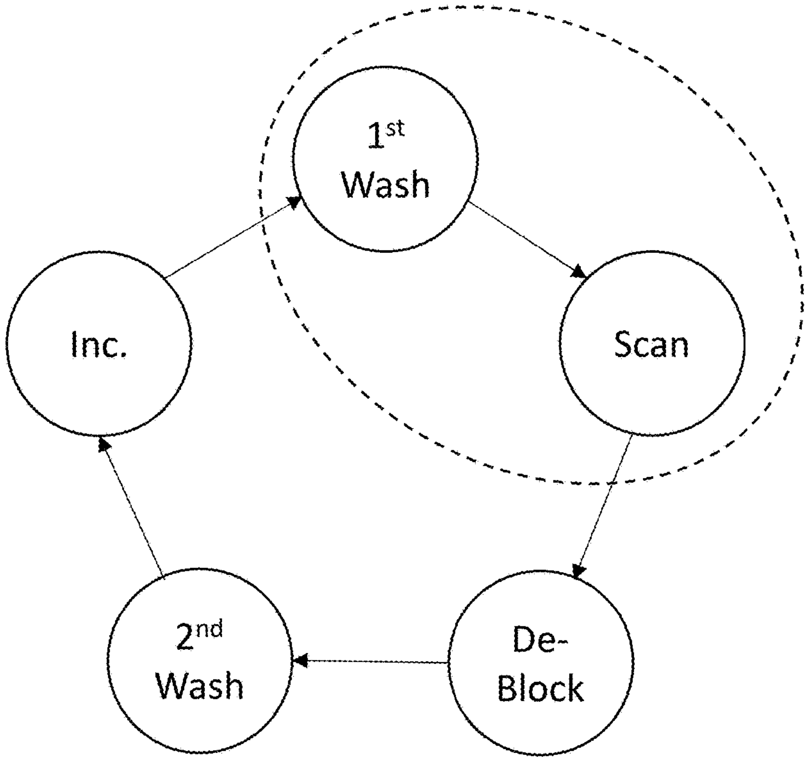

Referring now to FIGS. 1-3, overviews of some steps in SBS processes are shown. Specifically, the compositions employed at different stages of the SBS process are shown. The compositions include an incorporation composition (Inc.) used in an incorporation step, a scan composition (Scan) used in an identification step, a de-blocking composition (De-Block) used in a deblocking step, and a first wash composition ($1^{st}$ wash) used in a first wash step, and optionally a second wash composition ($2^{nd}$ wash) used in a second wash step. One or more additional wash steps (not shown) may be performed. The second wash composition ($2^{nd}$ wash) and other additional wash compositions, if used, are preferably free of a polymerase. The second wash composition ($2^{nd}$ wash) and the other additional wash compositions, if used, are preferably free of a nucleotides.

The first wash ($1^{st}$ wash) composition may comprise one or more components of the de-block composition (De-Block) as indicated by the dashed ellipses in FIG. 1 and FIG. 2. Thus, the first wash ($1^{st}$ wash) composition may be used in the de-blocking step.

The first wash ($1^{st}$ wash) composition may comprise one or more components of the scan composition (Scan) as indicated by the dashed ellipse in FIG. 3. Thus, the first wash ($1^{st}$ wash) composition may be used in the identification step.

It will be understood that a wash composition may be incubated with the template and copy strands for a period of time rather than continuously flowing the first wash composition past the template and copy polynucleotide strands. Of course, the wash composition may be continuously flowed past the template and copy polynucleotide strands.

The incorporation composition (Inc.) comprises a plurality of blocked, labeled nucleotides and may include a first polymerase. The blocked, labeled nucleotides are incubated with the template strands and the first polymerase in an incorporation step to incorporate an appropriate nucleotide into a copy strand based on the sequence of the template strand.

The blocked, labeled nucleotides in the incorporation composition comprise a blocking moiety and a labeled moiety. In some embodiments, the blocking moiety may be the labeled moiety. The blocking moiety, the labeled moiety, or the blocking moiety and the labeled moiety molecule may be linked to the nucleotide by any suitable linker. The linker may comprise one or more cleavable groups including, but not limited to, disulfide, diol, diazo, ester, sulfone azide, alyl and silyl ether, azide and alkoxy groups. In preferred embodiments, the linker comprises one or more of an azide, an alkoxy, and a disulfide group as a linker. Incorporation of a disulfide bond into a linker may be accomplished in a number of ways, for example as described in U.S. Pat. No. 7,771,973 or as described in Hermanson, Bioconjugate Techniques, Second Edition, Academic Press (incorporated herein by reference in their entireties).

More generally, suitable linkers include, but are not limited to, disulfide linkers, acid labile linkers (including dialkoxybenzyl linkers, Sieber linkers, indole linkers, and t-butyl Sieber linkers), electrophilically cleavable linkers, nucleophilically cleavable linkers, photocleavable linkers, cleavage under reductive conditions, oxidative conditions, cleavage via use of safety-catch linkers, and cleavage by elimination mechanisms.

Any suitable electrophilically cleavable linkers may be employed. Electrophilically cleavable linkers are typically cleaved by protons and include cleavages sensitive to acids. Suitable electrophilically cleavable linkers include the modified benzylic systems such as trityl, p-alkoxybenzyl esters and p-alkoxybenzyl amides. Other suitable electrophilically cleavable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable electrophilically cleavable linkers molecules.

Any suitable nucleophilic cleavage linker may be employed. Nucleophilic cleavage is a well-recognized method in the preparation of linker molecules. Groups such as esters that are labile in water (i.e., can be cleaved simply at basic pH) and groups that are labile to non-aqueous nucleophiles, may be used. Fluoride ions may be used to cleave silicon-oxygen bonds in groups such as triisopropyl silane (TIPS) or t-butyldimethyl silane (TBDMS).

Any suitable photocleavable linker may be used. Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry may also be used (Lee et al., J. Org. Chem. 64:3454-3460, 1999).

Any suitable linker that cleaves under reductive conditions may be used. There are known many linkers that are susceptible to reductive cleavage. For example, catalytic hydrogenation using palladium-based catalysts has been used to cleave benzyl and benzyloxycarbonyl groups. By way of further example, disulfide bond reduction is also known in the art.

Any suitable linker that cleaves under oxidative conditions may be used. Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the invention.

Any suitable safety-catch linker may be used. Safety-catch linkers are those that cleave in two steps. In a preferred system, the first step is the generation of a reactive nucleophilic center followed by a second step involving an intramolecular cyclization that results in cleavage. For example, levulinic ester linkages may be treated with hydrazine or photochemistry to release an active amine, which may then be cyclized to cleave an ester elsewhere in the molecule (Burgess et al., J. Org. Chem. 62:5165-5168, 1997).

Any suitable linker that may be cleaved by elimination mechanisms may be used. For example, the base-catalyzed elimination of groups such as Fmoc and cyanoethyl, and palladium-catalyzed reductive elimination of allylic systems, may be used.

The linkers may include one or more spacer in addition to the cleavage site. The spacer distances e.g., the nucleotide base from the cleavage site or label or blocking moiety. The length of the linker is generally not important provided that the nucleotide may be incorporated into the copy strand after by a chain extending enzyme after the blocking moiety is cleaved.

Examples of suitable linkers, nucleotides, blocking moieties that may be employed are described in U.S. Pat. No. 7,541,444; WO 03/048387; US 2013/0079232A1; and U.S. Pat. No. 7,414,116, each of which is hereby incorporated herein in their respective entireties to the extent that they do not conflict with the present disclosure. Particularly preferred linkers are phosphine-cleavable azide containing linkers. The labeled moiety may comprise a fluorophore.

The skilled person will appreciate how to attach a suitable blocking group to a ribose ring of a nucleotide to block interactions with the 3'-OH. The blocking group may be attached directly at the 3' position or may be attached at the 2' position (the blocking group being of sufficient size or charge to block interactions at the 3' position). Alternatively, the blocking group may be attached at both the 3' and 2' positions and may be cleaved to expose the 3'OH group.

Suitable blocking groups will be apparent to the skilled person and may be formed from any suitable protecting group disclosed in "Protective Groups in Organic Synthesis", T. W. Greene and P. G. M. Wuts, 3rd Ed., Wiley Interscience, New York, which is hereby incorporated herein by reference in its entirety to the extent that it does not conflict with the present disclosure. The blocking group is preferably removable (or modifiable) to produce a 3' OH group. The process used to obtain the 3' OH group may be any suitable chemical or enzymic reaction.

Blocking moieties may be as described in U.S. Pat. No. 7,414,116, which is hereby incorporated herein by reference in its entirety to the extent that it does not conflict with the present disclosure.

The duration of an incorporation step may be reduced when a sequencing cycle includes a wash step that includes the first wash composition. The duration of the incorporation step may be reduced by 10% or more, 20% or more, 30% or more, 40% or more, or 50% or more relative to the duration of an incorporate step in a substantially similar sequencing cycle that does not include a wash step that includes a first wash composition. The duration of the incorporation step may be reduced while achieving the same or substantially similar sequencing accuracy. As an example, an incorporation step may be reduced from 25 seconds without a wash step that includes a first wash composition to 10 seconds with a wash step that includes a first wash composition. In some embodiments, the incorporation step may be 20 seconds or less, 15 seconds or less, 10 seconds, or less, or 5 seconds or less.

Following the incorporation step, the unincorporated blocked, labeled nucleotides may be washed away using a wash composition (not shown) and the identity of the nucleotide incorporated into the copy strand can be determined. A scan composition (Scan) is present during detection of the identity of the incorporated blocked, labeled nucleotide. The scan composition may comprise an antioxidant to protect the template strand and the copy strand from damage that may be induced by light during the detection step. See, e.g., U.S. Pat. Nos. 9,115,353 and 9,217,178, which are hereby incorporated herein by reference in their respective entireties to the extent that they do not conflict with the present disclosure. A universal wash composition (not shown) may be employed to wash away the unincorporated blocked, labeled nucleotides prior to introduction of the scan composition, the first wash composition ($1^{st}$ wash) may be employed to wash away the unincorporated blocked, labeled nucleotides prior to introduction of the scan composition (e.g., as shown in FIG. 3), or the introduction of the scan composition (Scan) may serve to wash away the unincorporated blocked, labeled nucleotides.

Following the identification step, the template and copy polynucleotide strands may be incubated with the first wash composition ($1^{st}$ wash) as indicated in FIG. 2. Regardless of whether a first wash step occurs after the scan step, the blocking moiety and the labeled moiety may be removed from the nucleotide incorporated into the copy strand by introducing a de-blocking composition (De-Block). The de-blocking composition (De-Block) may comprise a cleavage agent. Preferably, cleavage agent removes both the blocking moiety and the labeled moiety. For example, the labeled moiety may serve as the blocking moiety, the labeled moiety may be on the blocking moiety, the labeled moiety may be attached to the nucleotide by the same linker as the blocking moiety, etc.

In some embodiments, the blocking moiety is chemically removed. For purposes of the present disclosure, "chemical" removal of a blocking moiety involves a chemical reaction between a cleavage agent and the blocked nucleotide to cause the blocking moiety to be removed from the nucleotide. Preferably the blocking moiety and the labeled moiety are both cleaved by the same process when blocking moiety and the labeled moiety are separate moieties. For example, the blocking moiety and the labeled moiety may be bound to the nucleotide by the same or similar linking groups, which may be cleaved or removed by the same reagents or conditions. This will make the deblocking and de-labeling process more efficient, as only a single treatment will be required to remove both the label and the block. The blocking moiety and the labeled moiety may, of course, be cleaved under entirely different chemical conditions and the de-block composition may comprise a separate cleavage agent for removing the labeled moiety.

The de-blocking composition may comprise any suitable cleavage agent. The cleavage agent may depend on the cleavage group present. For example, cleavage of disulfide bonds or other reductive cleavage groups may be accomplished by a reducing agent. Reduction of a disulfide bond results in the release of the linked molecule from the nucleotide. Reducing agents useful in practicing embodiments as described herein include, but are not limited to, phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol and tris(2-carboxyethyl)phosphine (TCEP), tris(hydroxymethyl)phosphine (THP) and β-[tris(hydroxymethyl)phosphine]propionic acid (THPP). In some embodiments, a reducing agent used for cleaving a disulphide bond in a linker as described herein is DTT. In some embodiments, the concentration of a reducing reagent, for example DTT, utilized for cleaving a disulfide bond is at least 1 to 1000 mM, at least 20 to 800 mM, at least 40 to 500 mM, and preferably at least 50 to 200 mM.

In some embodiments, a reducing agent used for cleaving a disulphide bond in a linker or a cleavable linker comprising an allyl or azido group is a phosphine reagent, a water-soluble phosphine reagent, a nitrogen containing phosphine reagent and salts and derivatives thereof. Exemplary phosphine reagents include, but are not limited to, tris(2-carboxyethyl)phosphine (TCEP), tris(hydroxypropyl) phosphine (THP), tris(hydroxymethyl)phosphine (TMP) and those disclosed in US patent publication 2009/0325172 (incorporated herein by reference in its entirety) such as triaryl phosphines, trialkyl phosphines, sulfonate containing and carboxylate containing phosphines and derivatized water soluble phosphines. Other phosphines that may be used as cleavage agents include those described in U.S. Pat. No. 7,414,116, which is hereby incorporated herein by reference in its entirety to the extent that it does not conflict with the present disclosure. In some embodiments, the concentration of a phosphine utilized is from about 0.5 mM to about 500 mM, such as from about 5 mM to about 50 mM, and preferably from about 10 mM to about 40 mM. Methods and compositions as described herein are not limited by any particular cleavage group and alternatives will be readily apparent to a skilled artisan and are considered within the scope of the present disclosure.

After the de-blocking step, the removed blocking moiety and cleavage agent are washed away with a wash composition, such as the first wash composition ($1^{st}$ Wash) as shown in FIG. 1 or a second wash composition ($2^{nd}$ Wash) as shown in FIGS. 2-3, and the process may be repeated. At least one wash composition (e.g., the first or second wash composition) used following a de-block step may comprise a scavenger, such as described above regarding the first wash composition.

In some embodiments where the second wash composition is used following the de-block step, the second wash composition and the scan composition may be the same. For example, a "ScavScan" composition as described in U.S.

Patent Application Publication No. 2020/0190569 A1 may serve as both the Scan composition and the second was composition. Such a composition may comprise an antioxidant to reduce potential photo-induced damage during the scanning step and a scavenger to interact with reactive compounds in or resulting from the de-blocking step.

Additional wash steps, which may employ a universal wash composition, the second wash composition, or another suitable wash composition, may be employed between any steps illustrated in FIGS. 1-3.

In some embodiments, cartridges for use with sequencing apparatus, such as sequencing instruments, may include a chamber from which one or more compositions may be withdrawn or expelled for use in a sequencing. For example and with reference to FIG. 4, a cartridge 100 comprising a plurality of chambers 110, 120, 130, 140, 150, 160 is shown. The cartridge 100 may include fluid coupling ports, valves, or the like for operably coupling the chambers 110, 120, 130, 140, 150, 160 to the sequencing instrument. Each chamber 110, 120, 130, 140, 150, 160 may contain a single composition. The compositions in the chambers 110, 120, 130, 140, 150, 160 may be fluid compositions at room temperature or ambient operating temperature of the sequencing instrument. Preferably, the cartridge 100 and sequencing instrument are configured such that the sequencing instrument may selectively withdraw or expel a composition from each chamber 110, 120, 130, 140, 150, 160 of the cartridge 100.

An incorporation composition comprising reagents for incorporating a blocked, labeled nucleotide into a copy polynucleotide strand complementary to at least a portion of a template polynucleotide strand (e.g., an Inc. composition as shown in, and discussed above regarding, FIGS. 1-3) may be disposed in the first chamber 110. The incorporation composition in the first chamber 110 may comprise a plurality of blocked, labeled nucleotides. The incorporation composition in the first chamber 110 may comprise a first polymerase.

A detection composition for use in a step of identifying the blocked, labeled nucleotide incorporated into a copy polynucleotide strand (e.g., a Scan composition as shown in, and discussed above regarding, FIGS. 1-3) may be disposed in the second chamber 120. The detection composition disposed in the second chamber 120 may comprise an antioxidant.

A cleavage composition comprising one or more reagent for removing a label and blocking moiety from the blocked, labeled nucleotide incorporated into the copy strand (e.g., a De-Block composition as shown in, and discussed above regarding, FIGS. 1-3) may be disposed in the third chamber 130. The cleavage composition in the third chamber 130 may comprise a cleavage agent.

A first wash composition for washing reagents or components from a previous step in a sequencing cycle (e.g., a $1^{st}$ Wash composition as shown in, and discussed above regarding, FIGS. 1-3) may be disposed in the fourth chamber 140. The first wash composition in the fourth chamber 140 may comprise a second polymerase. The first wash composition may comprise a plurality of nucleotides. The nucleotides may be blocked, labeled, or blocked and labeled. The first wash composition may be configured to prevent the second polymerase from incorporating one of the plurality of nucleotides into the copy polynucleotide strand. The first wash composition may be substantially free of $Mg^{2+}$ or free of $Mg^{2+}$.

A second wash composition for washing reagents or components from a previous step in a sequencing cycle (e.g., a 2nd Wash composition as shown in, and discussed above regarding, FIGS. 2-3) may be disposed in the fifth chamber 150. The second wash composition in the fifth chamber 140 is preferably free from a polymerase and nucleotides. The second wash composition may comprise a scavenger. In some embodiments, the second wash composition may comprise an antioxidant and may also be used as the detection composition.

A universal wash composition may be disposed in the sixth chamber 160. The universal wash composition may be used for any additional wash steps that may be needed or desired in carrying out a sequencing method by a sequencing instrument.

Figure 4:
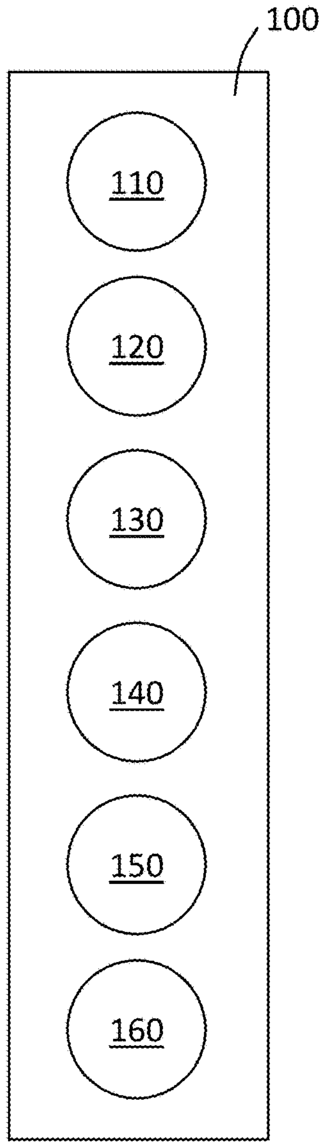
FIG. 4 is a schematic top plan view of a cartridge including compositions for sequencing in accordance with various embodiments disclosed herein.

The cartridge 100 shown in FIG. 4 may comprise any suitable number of chambers 110, 120, 130, 140, 150, 160, which may contain any suitable composition. It should be understood that a cartridge may comprise more or less chambers than depicted in FIG. 4 and that the compositions described above regarding FIG. 4 are merely examples of compositions that may be contained in chambers of a cartridge.

In some embodiments, a kit for use with a sequencing apparatus, such as a sequencing instrument, may include containers from which one or more compositions may be withdrawn or expelled for use in a sequencing. For example and with reference to FIG. 5, a kit 190 comprising a plurality of containers 191, 192, 193, 194, 195, 196 is shown. Each container 191, 192, 193, 194, 195, 196 may contain a single composition. The compositions may be fluid compositions at room temperature or ambient operating temperature of the sequencing apparatus. The containers 191, 192, 193, 194, 195, 196 may be configured to fluidly couple to the sequencing apparatus such that the compositions in the containers 191, 192, 193, 194, 195, 196 may be withdrawn or expelled by the sequencing apparatus.

Container 191 may contain an incorporation composition as described above. Container 192 may contain detection composition as described above. Container 193 may contain cleavage composition as described above. Container 194 may contain a first wash composition as described above. Container 195 may contain a second wash composition as described above. Container 196 may contain a universal wash composition as described above.

The kit may comprise instructions for using the kit. For example, the kit may comprise instructions for using one or more of the containers, such as how to operatively couple the containers to sequencing apparatus, how to fill chambers of a cartridge with contents of the containers, when compositions in the containers are employed in a sequencing reaction, or the like.

Figure 5:
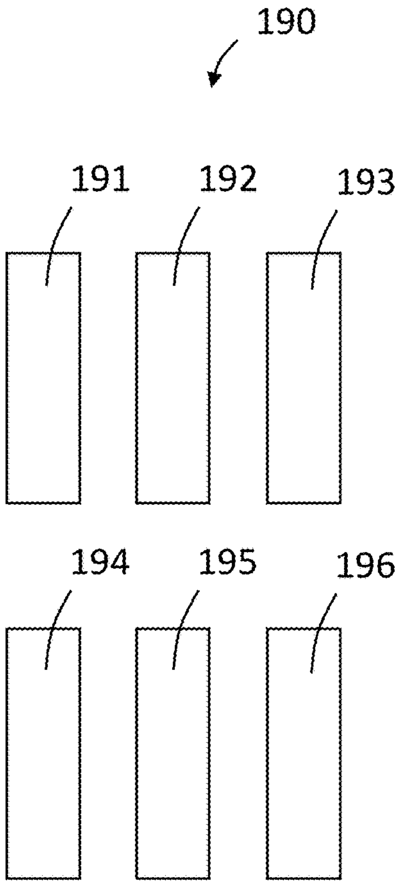
FIG. 5 is a schematic side plan view of a kit including containers containing comprising compositions for sequencing in accordance with various embodiments disclosed herein.

The kit 190 shown in FIG. 5 may comprise any suitable number of containers 191, 192, 193, 194, 195, 196, which may contain any suitable composition. It should be understood that a kit may comprise more or less containers than depicted in FIG. 5 and that the compositions described above regarding FIG. 5 are merely examples of compositions that may be contained in the containers of the kit.

The sequencing methods described herein may be performed in any suitable manner, using any suitable apparatus. In some embodiments, the sequencing methods employ a solid support on which the multiple template polynucleotide strands are immobilized. The term immobilized as used herein is intended to encompass direct or indirect attachment to a solid support via covalent or non-covalent bond(s). In particular embodiments, all that is required is that the polynucleotides remain immobilized or attached to a support under conditions in which it is intended to use the support, for example in applications requiring nucleic acid amplification and/or sequencing. For example, oligonucleotides or primers may be immobilized such that a 3' end is available for enzymatic extension and/or at least a portion of the sequence is capable of hybridizing to a complementary sequence. Immobilization can occur via hybridization to a surface attached primer, in which case the immobilized primer or oligonucleotide may be in the 3'-5' orientation. Alternatively, immobilization may occur by non-base-pairing hybridization, such as covalent attachment.

By way of example, the polynucleotides may be attached to the surface by hybridization or annealing to one or more primers in a patch of primers. Hybridization may be accomplished, for example, by ligating an adapter to the ends of the template polynucleotides. The nucleic acid sequence of the adapter can be complementary to the nucleic acid sequence of the primer, thus, allowing the adapter to bind or hybridize to the primer on the surface. Optionally, the polynucleotides may be single- or double-stranded and adapters may be added to the 5' and/or 3' ends of the polynucleotides. Optionally, the polynucleotides may be double-stranded, and adapters may be ligated onto the 3' ends of double-stranded polynucleotide. Optionally, polynucleotides may be used without any adapter. In some embodiments, template polynucleotides may be attached to a surface by interactions other than hybridization to a complementary primer. For example, a polynucleotide may be covalently attached to a surface using a chemical linkage such as those resulting from click chemistry or a receptor-ligand interaction, such as streptavidin-biotin binding.

Primer oligonucleotides, oligonucleotide primers and primers are used throughout interchangeably and are polynucleotide having sequences that are capable of annealing specifically to one or more polynucleotide templates to be amplified or sequenced. Generally, primer oligonucleotides are single-stranded or partially single-stranded. Primers may also contain a mixture of non-natural bases, non-nucleotide chemical modifications or non-natural backbone linkages so long as the non-natural entities do not interfere with the function of the primer. Optionally, a patch of primers on a surface of a solid support may comprise one or more different pluralities of primer molecules. By way of example, a patch may comprise a first, second, third, fourth, or more pluralities of primer molecules each plurality having a different sequence. It will be understood that for embodiments having different pluralities of primers in a single patch, the different pluralities of primers may share a common sequence so long as there is a sequence difference between at least a portion of the different pluralities. For example, a first plurality of primers may share a sequence with a second plurality of primers as long the primers in one plurality have a different sequence not found in the primers of the other plurality.

The template polynucleotides may be amplified on the surface of the solid support. Polynucleotide amplification includes the process of amplifying or increasing the numbers of a polynucleotide template and/or of a complement thereof that are present, by producing one or more copies of the template and/or or its complement. Amplification may be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010251; which are incorporated by reference herein in their entireties. Briefly, in the provided methods, amplification can occur on the surface to which the polynucleotide molecules are attached. This type of amplification can be referred to as solid phase amplification, which when used in reference to polynucleotides, refers to any polynucleotide amplification reaction carried out on or in association with a surface (e.g., a solid support). Typically, all or a portion of the amplified products are synthesized by extension of an immobilized primer. Solid phase amplification reactions are analogous to standard solution phase amplifications except that at least one of the amplification primers is immobilized on a surface (e.g., a solid support).

Suitable conditions include providing appropriate buffers/solutions for amplifying polynucleotides. Such solutions include, for example, an enzyme with polymerase activity, nucleotide triphosphates, and, optionally, additives such as DMSO or betaine. Optionally, amplification is carried out in the presence of a recombinase agent as described in U.S. Pat. No. 7,485,428, which is incorporated by reference herein in its entirety, which allows for amplification without thermal melting. Briefly, recombinase agents such as the RecA protein from *E. coli* (or a RecA relative from other phyla), in the presence of, for example, ATP, dATP, ddATP, UTP, or ATPγS, will form a nucleoprotein filament around single-stranded DNA (e.g., a primer). When this complex comes in contact with homologous sequences the recombinase agent will catalyze a strand invasion reaction and pairing of the primer with the homologous strand of the target DNA. The original pairing strand is displaced by strand invasion leaving a bubble of single stranded DNA in the region, which serves as a template for amplification.

Solid-phase amplification may comprise a polynucleotide amplification reaction comprising only one species of oligonucleotide primer immobilized to a surface. Alternatively, the surface may comprise a plurality of first and second different immobilized oligonucleotide primer species. Solid phase nucleic acid amplification reactions generally comprise at least one of two different types of nucleic acid amplification, interfacial and surface (or bridge) amplification. For instance, in interfacial amplification the solid support comprises a template polynucleotide that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide that remains attached to the solid support. After the extension phase, the polynucleotides (e.g., template and its complementary product) are denatured such that the template polynucleotide is released into solution and made available for hybridization to another immobilized oligonucleotide primer. The template polynucleotide may be made available in 1, 2, 3, 4, 5 or more rounds of primer extension or may be washed out of the reaction after 1, 2, 3, 4, 5 or more rounds of primer extension.

In surface (or bridge) amplification, an immobilized polynucleotide hybridizes to an immobilized oligonucleotide primer. The 3' end of the immobilized polynucleotide provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Amplification may be used to produce colonies of immobilized polynucleotides. For example, the methods can produce clustered arrays of polynucleotide colonies, analogous to those described in U.S. Pat. No. 7,115,400; U.S. Publication No. 2005/0100900; WO 00/18957; and WO 98/44151, which are incorporated by reference herein in their entireties. "Clusters" and "colonies" are used interchangeably and refer to a plurality of copies of a polynucleotide having the same sequence and/or complements thereof attached to a surface. Typically, the cluster comprises a plurality of copies of a polynucleotide having the same sequence and/or complements thereof, attached via their 5' termini to the surface. The copies polynucleotides making up the clusters may be in a single or double stranded form.

Thus, the plurality of template polynucleotides may be in a cluster, each cluster containing template polynucleotides of the same sequence. A plurality of clusters can be sequenced, each cluster comprising polynucleotides of the same sequence. Optionally, the sequence of the polynucleotides in a first cluster is different from the sequence of the nucleic acid molecules of a second cluster. Optionally, the cluster is formed by annealing to a primer on a solid surface a template polynucleotide and amplifying the template polynucleotide under conditions to form the cluster comprising the plurality of template polynucleotides of the same sequence. Amplification can be thermal or isothermal.

Each colony may comprise polynucleotides of the same sequences. In particular embodiments, the sequence of the polynucleotides of one colony is different from the sequence of the polynucleotides of another colony. Thus, each colony comprises polynucleotides having different nucleic acid sequences. All the immobilized polynucleotides in a colony are typically produced by amplification of the same polynucleotide. In some embodiments, it is possible that a colony of immobilized polynucleotides contains one or more primers without an immobilized polynucleotide to which another polynucleotide of different sequence may bind upon additional application of solutions containing free or unbound polynucleotides. However, due to the lack of sufficient numbers of free primers in a colony, this second or invading polynucleotide may not amplify to significant numbers. The second or invading polynucleotide typically is less than 1, 0.5, 0.25, 0.1, 0.001 or 0.0001% of the total population of polynucleotides in a single colony. Thus, the second or invading polynucleotide may not be optically detected or detection of the second or invading polynucleotide is considered background noise or does not interfere with detection of the original, immobilized polynucleotides in the colony. In such embodiments, the colony will be apparently homogeneous or uniform in accordance with the resolution of the methods or apparatus used to detect the colony.

The clusters may have different shapes, sizes and densities depending on the conditions used. For example, clusters may have a shape that is substantially round, multi-sided, donut-shaped or ring-shaped. The diameter or maximum cross section of a cluster may be from about 0.2 μm to about 6 μm, about 0.3 μm to about 4 μm, about 0.4 μm to about 3 μm, about 0.5 μm to about 2 μm, about 0.75 μm to about 1.5 μm, or any intervening diameter. Optionally, the diameter or maximum cross section of a cluster may be at least about 0.5 μm, at least about 1 μm, at least about 1.5 μm, at least about 2 μm, at least about 2.5 μm, at least about 3 μm, at least about 4 μm, at least about 5 μm, or at least about 6 μm. The diameter of a cluster may be influenced by a number of parameters including, but not limited to, the number of amplification cycles performed in producing the cluster, the length of the polynucleotide template, the GC content of the polynucleotide template, the shape of a patch to which the primers are attached, or the density of primers attached to the surface upon which clusters are formed. However, as discussed above, in all cases, the diameter of a cluster may be no larger than the patch upon which the cluster is formed. For example, if a patch is a bead, the cluster size will be no larger than the surface area of the bead. The density of clusters can be in the range of at least about $0.1/mm^2$, at least about $1/mm^2$, at least about $10/mm^2$, at least about $100/mm^2$, at least about $1,000/mm^2$, at least about $10,000/mm^2$ to at least about $100,000/mm^2$. Optionally, the clusters have a density of, for example, $100,000/mm^2$ to $1,000,000/mm^2$ or $1,000,000/mm^2$ to $10,000,000/mm^2$. The methods provided herein can produce colonies that are of approximately equal size. This occurs regardless of the differences in efficiencies of amplification of the polynucleotides of different sequence.

Clusters may be detected, for example, using a suitable imaging means, such as, a confocal imaging device or a charge coupled device (CCD) or CMOS camera. Exemplary imaging devices include, but are not limited to, those described in U.S. Pat. Nos. 7,329,860; 5,754,291; and 5,981,956; and WO 2007/123744, each of which is herein incorporated by reference in its entirety. The imaging apparatus may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information.

As used herein the term support refers to a substrate for attaching polynucleotides. A support is a material having a rigid or semi-rigid surface to which a polynucleotide can be attached or upon which nucleic acids can be synthesized and/or modified. Supports can include any resin, gel, bead, well, column, chip, flowcell, membrane, matrix, plate, filter, glass, controlled pore glass (CPG), polymer support, membrane, paper, plastic, plastic tube or tablet, plastic bead, glass bead, slide, ceramic, silicon chip, multi-well plate, nylon membrane, fiber optic, and PVDF membrane.

A support may include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight-channel flow cell used in the cBot sequencing workstation (Illumina, Inc., San Diego, CA). Exemplary flow cells are described in WO 2007/123744, which is incorporated herein by reference in its entirety. Optionally, the flowcell is a patterned flowcell. Suitable patterned flowcells include, but are not limited to, flowcells described in WO 2008/157640, which is incorporated by reference herein in its entirety.

A support may also include beads, including magnetic beads, hollow beads, and solid beads. Beads may be used in conjunction with flat supports, such flat supports optionally also containing wells. Beads, or alternatively microspheres, refer generally to a small body made of a rigid or semi-rigid material. The body may have a shape characterized, for example, as a sphere, oval, microsphere, or other recognized particle shape whether having regular or irregular dimensions. The sizes of beads, in particular, include, without limitation, about 1 μm, about 2 μm, about 3 μm, about 5 μm, about 10 μm, about 20 μm, about 30 μm, about 40 μm, about 60 μm, about 100 μm, about 150 μm or about 200 μm in diameter. Other particles may be used in ways similar to those described herein for beads and microspheres.

The composition of a support may vary depending, for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers IN, which is incorporated herein by reference. A support particle may be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication No. 02/0102578 and U.S. Pat. No. 6,429,027, both of which are incorporated herein by reference in their entirety.

Figure 6:
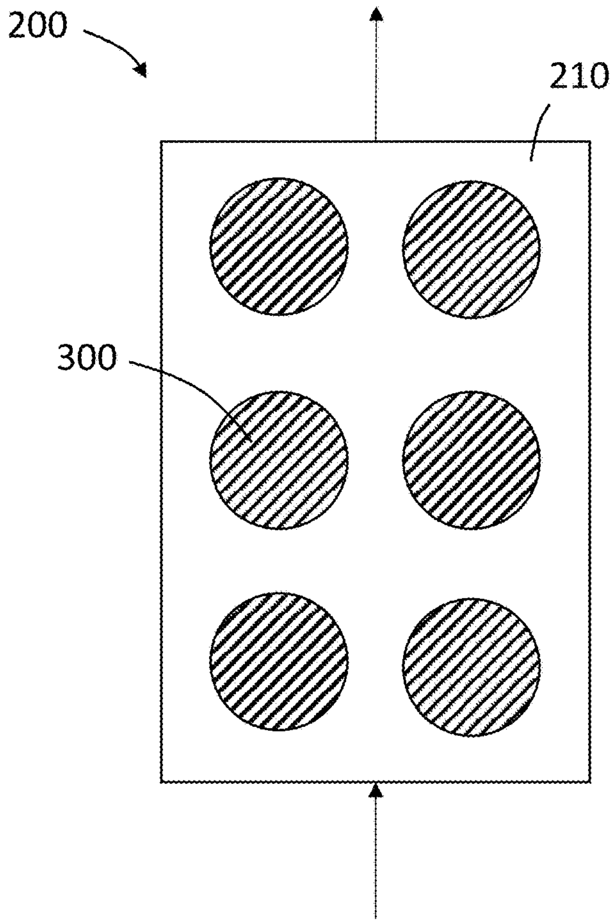
FIG. 6 is a schematic plan view of an embodiment of a flow cell that may be employed in accordance with the teachings presented herein.

For example, and with reference to FIG. 6, an embodiment of a solid support 200, such as a flow cell, is shown. The solid support 200 has a surface 210 to which clusters 300 containing multiple template polynucleotide strands having the same nucleotide sequence are immobilized relative to the surface 210 of the solid support 210. The surface 210 of the solid support 200 may be planar.

Fluid compositions containing reagents, wash buffers, and the like may flow over the surface 210 of the solid support 200 to interact with the template polynucleotides in the clusters 300. The flow of the compositions may occur in any direction, such as the direction indicated by the arrows in FIG. 6.

Sequencing apparatus with which the flow cell 300 may be used may be configured to flow compositions comprising reagents or washes across the surface 210 to interact with the template strands in the clusters 300. For example, the apparatus may cause polymerases, sequencing primers, nucleotides, wash compositions, cleavage agents, and the like to flow across the surface 210 of the solid support 200, such as a flow cell, to interact with the template polynucleotides in the clusters 300 at the appropriate times to carry out sequencing of the template strands.

Each cluster 300 may contain the same template polynucleotides or different polynucleotides than another cluster 300.

The template polynucleotides to be sequenced may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multicellular organism or single-celled organism such as a eukaryotic (including plants and algae) or prokaryotic organism, archaeon, microorganisms (e.g. bacteria, archaea, fungi, protists, viruses), and aquatic plankton.

Once the polynucleotides are obtained, a plurality of polynucleotides molecules of different sequence for use in the provided methods may be prepared using a variety of standard techniques available and known. Exemplary methods of polynucleotide molecule preparation include, but are not limited to, those described in Bentley et al., Nature 456:49-51 (2008); U.S. Pat. No. 7,115,400; and U.S. Patent Application Publication Nos. 2007/0128624; 2009/0226975; 2005/0100900; 2005/0059048; 2007/0110638; and 2007/0128624, each of which is herein incorporated by reference in its entirety. The template polynucleotides may contain a variety of sequences including, but not limited to, universal sequences and known or unknown sequences. For example, polynucleotide may comprise one or more regions of known sequence (e.g., an adaptor) located on the 5' and/or 3' ends. Such template polynucleotides may be formed by attaching adapters to the ends of a polynucleotides of unknown sequence. When the polynucleotides comprise known sequences on the 5' and 3' ends, the known sequences may be the same or different sequences. Optionally, a known sequence located on the 5' and/or 3' ends of the polynucleotides is capable of hybridizing to one or more primers immobilized on the surface. For example, a polynucleotide comprising a 5' known sequence may hybridize to a first plurality of primers while the 3' known sequence may hybridize to a second plurality of primers. Optionally, polynucleotides comprise one or more detectable labels. The one or more detectable labels may be attached to the polynucleotide template at the 5' end, at the 3' end, and/or at any nucleotide position within the polynucleotide molecule. The polynucleotides for use in the provided methods may comprise the polynucleotide to be amplified and/or sequenced and, optionally, short nucleic acid sequences at the 5' and/or 3' end(s).

A short nucleic acid sequence that is added to the 5' and/or 3' end of a polynucleotide may be a universal sequence. A universal sequence is a region of nucleotide sequence that is common to, i.e., shared by, two or more polynucleotides, where the two or more polynucleotides also have regions of sequence differences. A universal sequence that may be present in different members of a plurality of polynucleotides may allow the replication or amplification of multiple different sequences using a single universal primer that is complementary to the universal sequence. Similarly, at least one, two (e.g., a pair) or more universal sequences that may be present in different members of a collection of polynucleotides may allow the replication or amplification of multiple different sequences using at least one, two (e.g., a pair) or more single universal primers that are complementary to the universal sequences. Thus, a universal primer includes a sequence that may hybridize specifically to such a universal sequence. The polynucleotide may be modified to attach universal adapters (e.g., non-target nucleic acid sequences) to one or both ends of the different target sequences, the adapters providing sites for hybridization of universal primers. This approach has the advantage that it is not necessary to design a specific pair of primers for each polynucleotide to be generated, amplified, sequenced, and/or otherwise analyzed; a single pair of primers can be used for amplification of different polynucleotides provided that each polynucleotide is modified by addition of the same universal primer-binding sequences to its 5' and 3' ends.

The polynucleotides may also be modified to include any nucleic acid sequence desirable using standard, known methods. Such additional sequences may include, for example, restriction enzyme sites, or indexing tags in order to permit identification of amplification products of a given nucleic acid sequence.

As used herein, the term different when used in reference to two or more polynucleotides means that the two or more polynucleotides have nucleotide sequences that are not the same. For example, two polynucleotides can differ in the content and order of nucleotides in the sequence of one polynucleotide compared to the other polynucleotide. The term can be used to describe polynucleotides whether they are referred to as copies, amplicons, templates, targets, primers, oligonucleotides, or the like.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary. Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

EXAMPLES

During sequencing by synthesis (SBS), a substantial residual signal remains after the deblock step from the previous cycle of reversibly blocked, labeled nucleotide incorporation. The residual signal remains in clusters on the flow cell until the incorporation of the next reversibly blocked, labeled nucleotide. Washing with a standard wash composition is not able to eliminate the residual signal. The extent to which the dye (label) remaining in the clusters affects incorporation rates in the next cycle and affects other sequencing metrics was not well understood.

Inclusion of a wash step that includes a polymerase was effective in removing the residual signal. Improvements in sequencing metrics such as error rate, phasing, pre-phasing, and signal decay, were also observed. In addition, the inclusion of a wash step that includes a polymerase may allow shorter incorporation times.

Figure 7C:
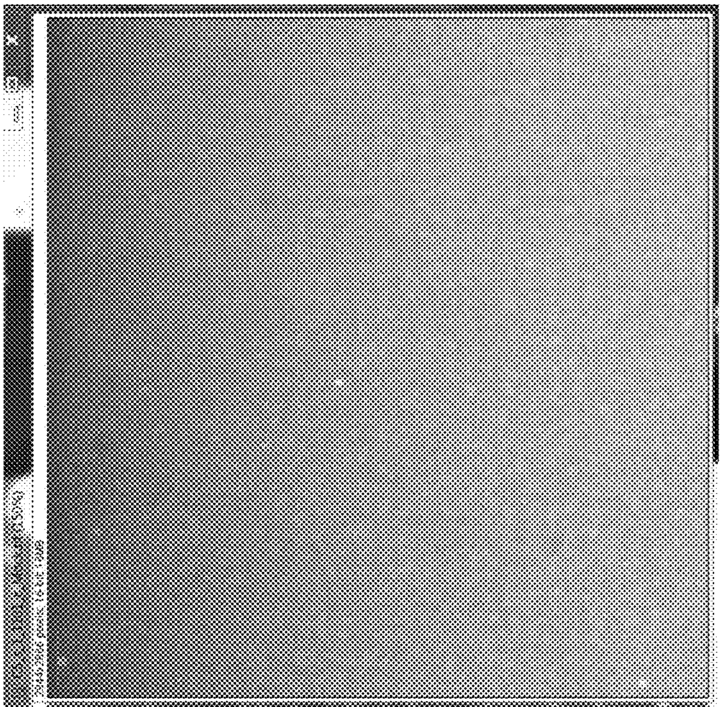
FIGS. 7A-7C are images from a sequencing run following an incorporation step (7A), following a deblock wash step (7B), and following a mock wash step, which included a first wash composition comprising a polymerase (7C).
Figure 7B:
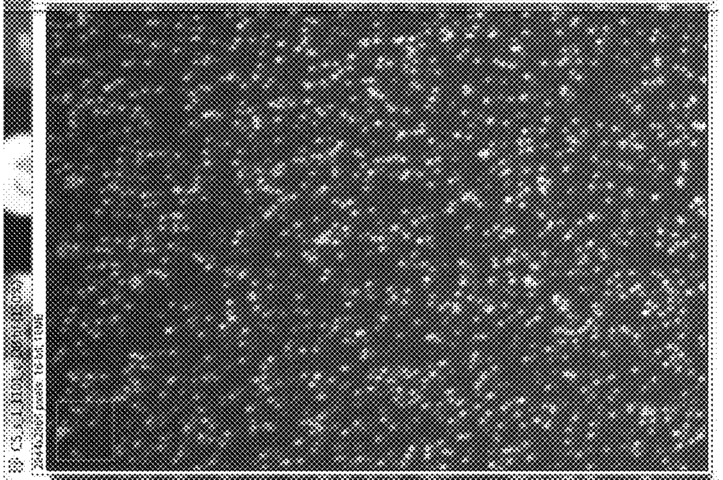
Figure 7A:
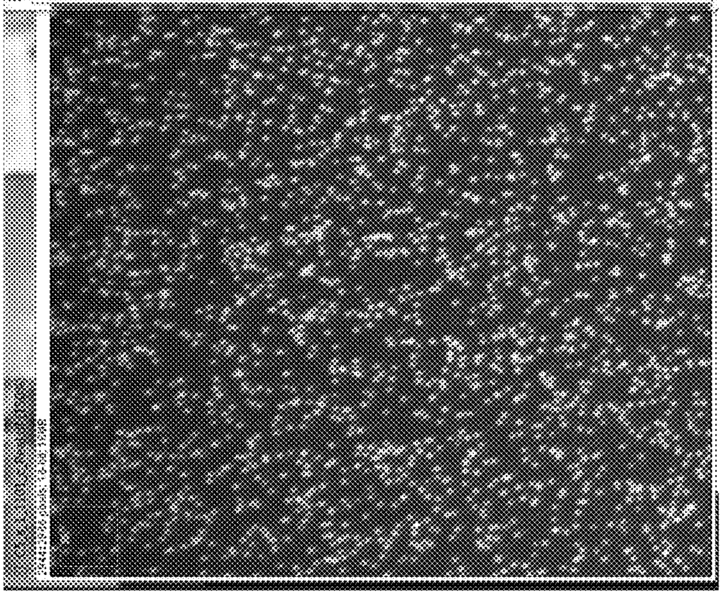

To determine whether a wash step including a polymerase can reduce background signal, the sequence of a known sequence was determined on an Illumina Model MiSeq sequencer using standard mixes, including a blue-green dye set, for the sequencer. An image was taken after an incorporation step, after a de-blocking step, and after a mock wash step. The mock wash step immediately followed the standard post-deblock wash. The mock wash composition was the same as the incorporation composition (included polymerase and incorporation buffer) except that the mock wash composition contained no fully functional nucleotides (ffNs) and contained no $Mg^{2+}$. Fifty microliters of mock wash composition was flushed through the flowcell with a 25 second incubation at 60° C. The resulting images are shown in FIG. 7A (following incorporation step), FIG. 7B (following deblock step), and FIG. 7C (following mock wash). A substantial amount of signal remained after the deblock wash. However, the mock wash, which included polymerase, removed all or nearly all the remaining signal.

To determine whether the residual signal remaining after the de-block step built up over time, a "blank" cycle was run every $10^{th}$ cycle. The incorporation mix in the blank cycle was identical to the incorporation mix in the normal cycles, except that the blank cycle incorporation mix lacked nucleotides. The incorporation mixes for the blank cycle and the normal cycles included a DNA polymerase (Pol 1901). Detection scans were run after each incorporation step (including the blank cycle) and after each de-blocking step. The sequencing was run on an Illumina Model MiSeq sequencer using a known target sequence and standard mixes, including a red-green dye set, for the sequencer.

No significant build-up of signal was observed (data not shown). That is, the residual signal was removed after each cycle of sequencing, and the blank cycle resulted in signal levels approaching background (data not shown). It was concluded that removal of residual signal following deblocking was not necessary, as the introduction of fresh incorporation mix (including fully functional nucleotides and polymerase) in a subsequent cycle removed the residual signal. It is noted that these initial tests were performed using a red-green dye set. It is anticipated that signal buildup may be an issue when using a blue-green dye set.

Figure 8:
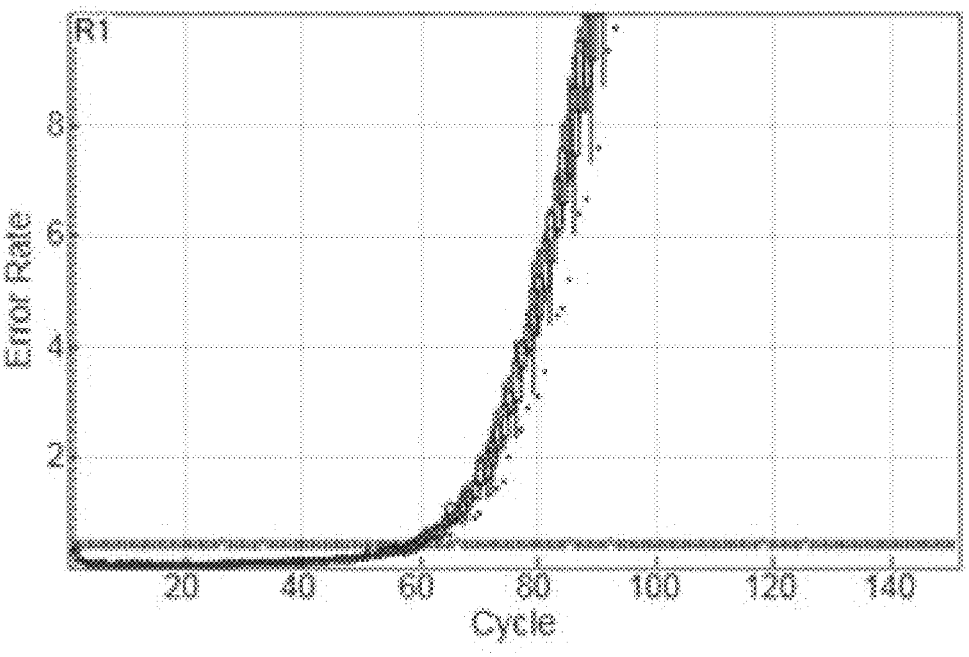
FIG. 8 is a plot of error rate versus cycle for a sequencing run in which a blank cycle was include as described in more detail in the Examples below.

The blank cycle was found to increase phasing and pre-phasing (approximately 0.6%). The increase in phasing and pre-phasing is believed to have resulted in base calling problems, which is believed to have led to an increase in error rate. A plot of error rate per cycle is shown in FIG. 8 when employing the blank cycle. Surprisingly, the blank cycle, which amounts effectively to a wash step employing the incorporation mix without nucleotides (but including polymerase), lead to increases in phasing, pre-phasing, and error rate.

Next, the effects of a "mock" incorporation composition, comprising a polymerase, fully functional nucleotides (ffNs), but no $Mg^{2+}$ was tested. The mock incorporation mix was identical to the incorporation mix used in normal incorporation cycles, except that the mock incorporation mix lacked $Mg^{2+}$. The incorporation mixes for the blank cycle and the normal cycles included a DNA polymerase (Pol 1901) and ffNs. Detection scans were run after each incorporation step (including the mock cycle) and after each de-blocking step. The mock incorporation mix was used as a wash composition following the deblocking step and immediately before the next round of incorporation. The sequencing was run on an Illumina Model MiSeq sequencer using a known target sequence and standard mixes for the sequencer, except that a blue-green dye set was used.

Figure 9:
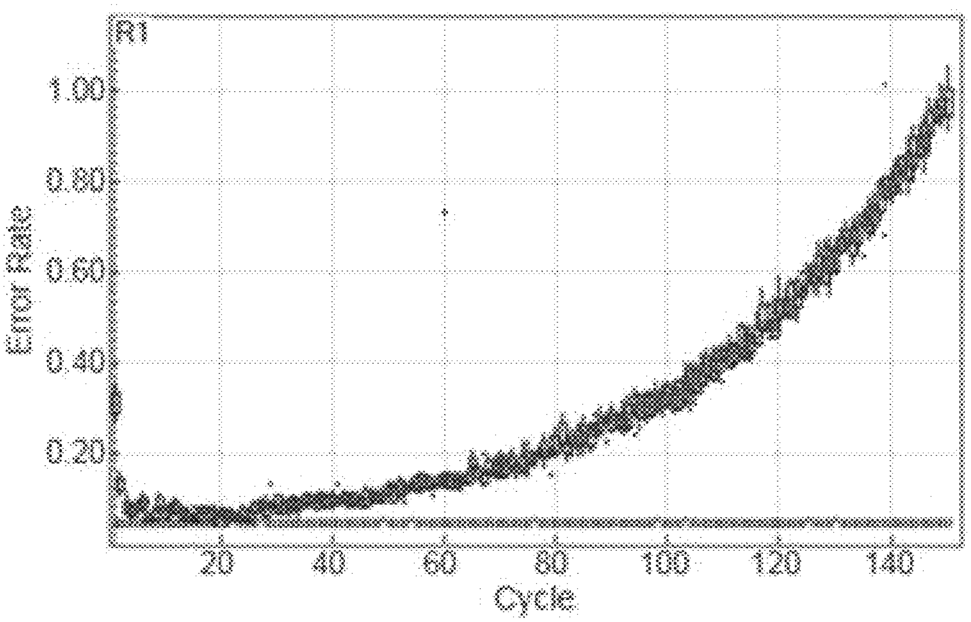
FIG. 9 is a plot of error rate versus cycle for a sequencing run in which a mock incorporation mix was step was included as described in more detail in the Examples below.

A plot of error rate per cycle is shown in FIG. 9 when employing the wash step with the mock incorporation mix.

Next, the effects of the incorporation of a wash step including a mock incorporation composition (as described above) was evaluated. The wash step including a mock incorporation composition was included each cycle between the deblock step and the post cleave wash step and compared to a normal sequencing run that did not include the mock wash step. The sequencing was run on an Illumina Model MiSeq sequencer using a known target sequence and standard mixes for the sequencer. Error rate and phasing were determined.

Figure 10:
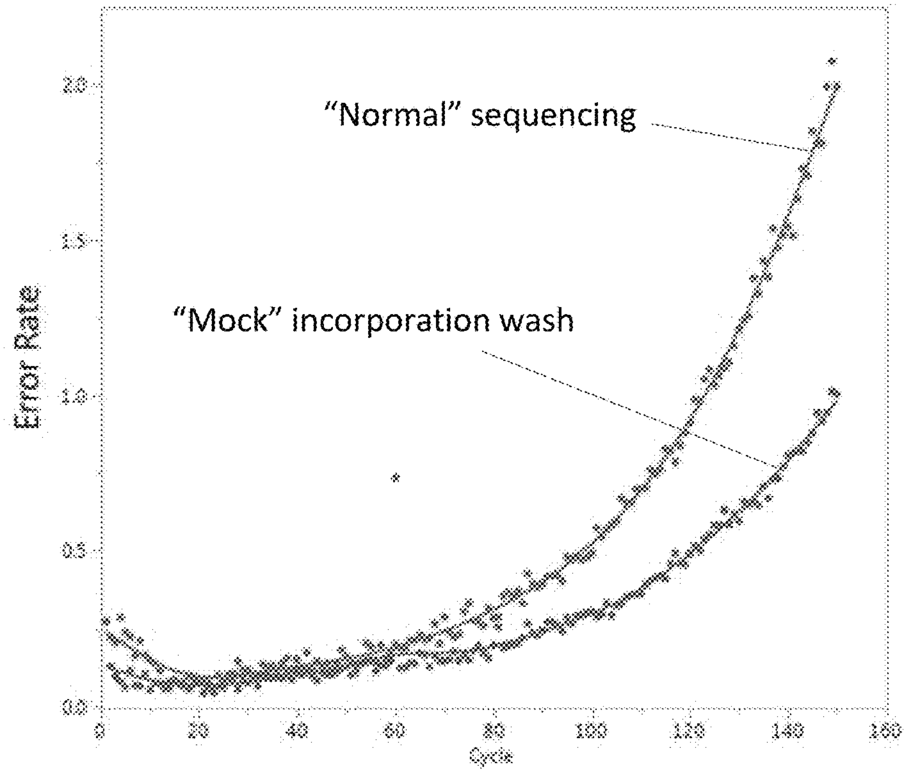
FIG. 10 is a plot of error rate versus cycle for a sequencing run in which a mock incorporation mix was step was included as described in more detail in the Examples below.
Figure 11:
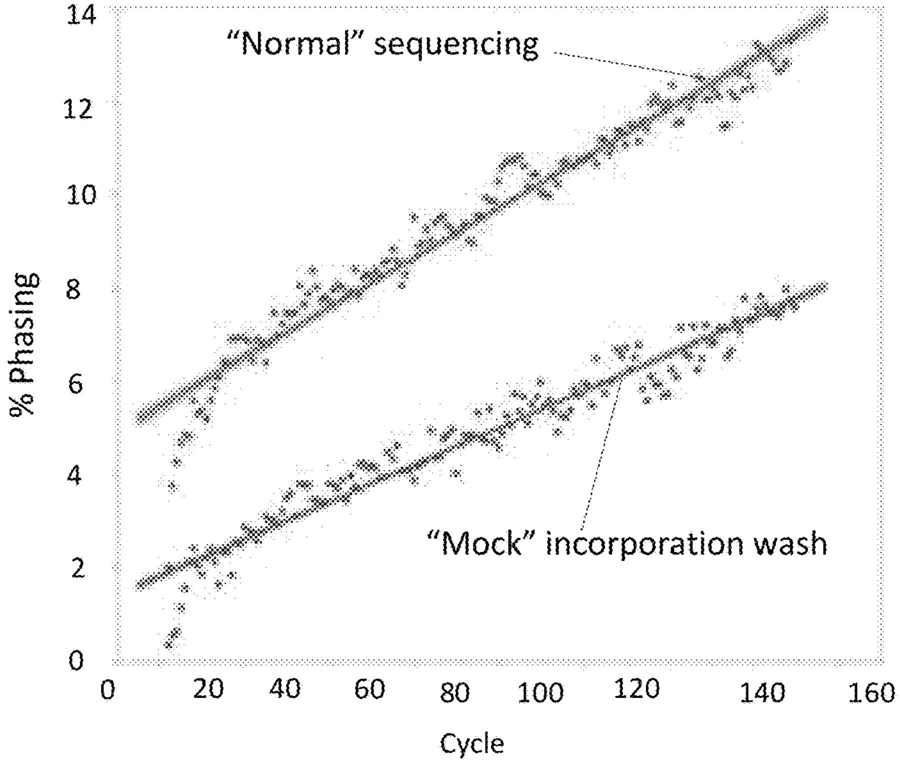
FIG. 11 is a plot of percent phasing versus cycle for a sequencing run in which a mock incorporation mix was step was included as described in more detail in the Examples below.

The error rate is shown in FIG. 10 and the phasing is shown in FIG. 11. As shown in FIGS. 10 and 11, the incorporation of the mock incorporation composition wash step resulted in lower error rate and lower percent phasing.

Figure 12:
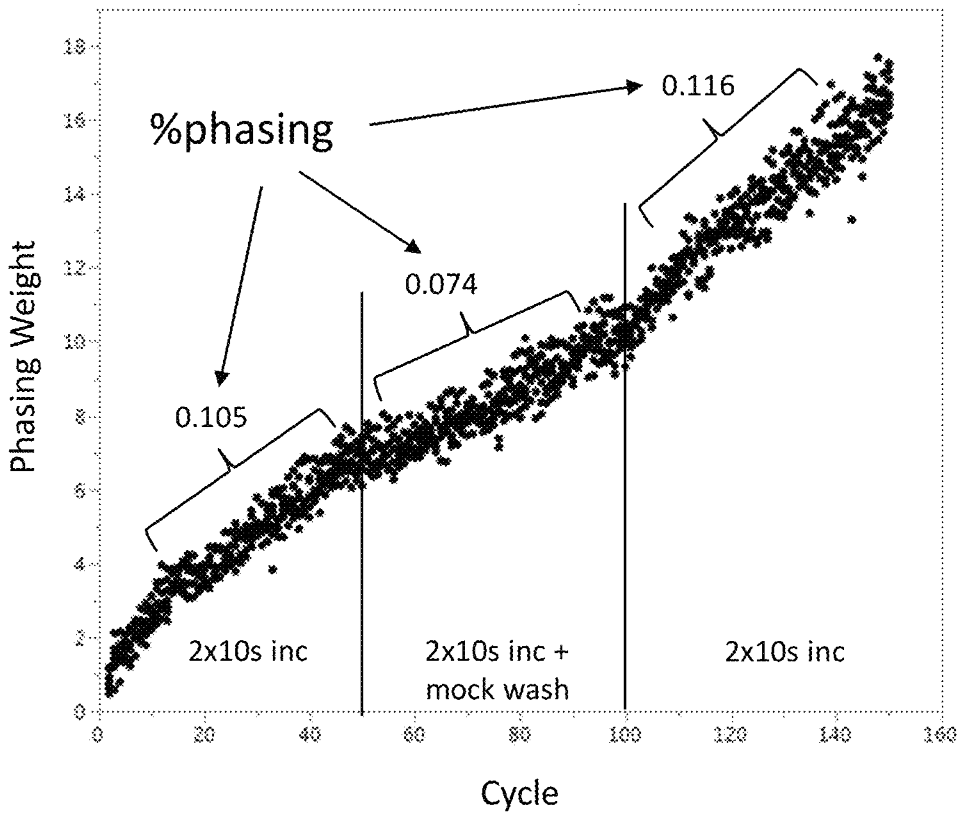
FIG. 12 is a plot of percent phasing versus cycle for a sequencing run in which 50 cycles included a mock incorporation step as described in more detail in the Examples below.

The effects of a "mock" wash step on sequencing metrics was determined. The mock wash composition was the same as the incorporation mix, except that the composition lacked ffNs and lacked $Mg^{2+}$. The mock wash step occurred immediately following the deblock wash step. For the mock wash step, 50 microliters of mock wash composition was flushed through the flowcell with a 25 second incubation at 60° C. Standard incorporation immediately followed the mock wash step. A known sequence was sequenced on an Illumina Model MiSeq sequencer using standard mixes (other than the mock wash step), including a blue-green dye set. The incorporation time was reduced from 2×25 seconds to 2×10 seconds. Standard sequencing with reduced incorporation step duration was run for 50 cycles, followed by 50 cycles that included a mock wash step, followed by 50 standard cycles. As indicated in FIG. 12, percent phasing was reduced (0.074) in the 50 cycles that included a mock wash step (compare to 0.105 in first 50 cycles) and increased when the mock wash step was no longer performed (0.116 for last 50 cycles).

The effects of a "mock" wash step on additional sequencing metrics was determined. The mock wash composition was the same as the incorporation mix, except that the composition lacked ffNs and lacked $Mg^{2+}$. The mock wash step occurred immediately following the deblock wash step. For the mock wash step, 50 microliters of mock wash composition was flushed through the flowcell with a 25 second incubation at 60° C. Standard incorporation immediately followed the mock wash step. A known sequence was sequenced on an Illumina Model MiSeq sequencer using standard mixes (other than the mock wash step), including a blue-green dye set. The incorporation time was reduced from 2×25 seconds to 2×10 seconds. Standard sequencing with reduced incorporation step duration was run for 150 cycles. Sequencing with a mock wash step was also run for 150 cycles. To stress the system and evaluate the effect of signal decay on increased light dose, the detection step included standard (1×) light dosing (standard exposure to blue and green), 5× light dosing (4× light dosing followed by 1× exposure for imaging), and 10× light dosing (9× light dosing followed by 1× for imaging). Percent phasing, percent pre-phasing, % error rate, and signal decay were evaluated. The mock wash resulted in no significant changes in signal decay (data not shown). The results on phasing, pre-phasing, and error rate are shown in Table 1 below.

TABLE 1

Comparison of metrics between standard and mock wash sequencing

| Conditions | % Phasing | | | % Pre-Phasing | % Error Rate 150 c | | |
|---|---|---|---|---|---|---|---|
| | 1X | 5X | 10X | 1X | 1X | 5X | 10X |
| Mock Wash | 0.14 | 0.16 | 0.19 | 0.11 | 0.41 | 0.52 | 0.75 |
| Standard | 0.25 | 0.27 | 0.29 | 0.10 | 0.56 | 0.83 | 1.47 |

As shown in Table 1, the mock was resulted in a decrease in phasing and a decrease in error rate. The reduction in phasing may be due to pre-binding of the polymerase during the mock wash step, speeding up the subsequent incorporation. The results in Table 1 suggest that shorter incorporation times may result in accurate sequencing if a mock wash step is included.

A number of embodiments have been described. Nevertheless, it will be understood that various modifications may be made. Accordingly, other embodiments are within the scope of the following claims.

What is claimed is:

1. A polynucleotide sequencing method comprising:

(a) incubating an incorporation composition comprising a first polymerase and a plurality of blocked, labeled nucleotides with a template polynucleotide strand such that the first polymerase incorporates one of the plurality of blocked, labeled nucleotides into a copy polynucleotide strand complementary to at least a portion of the template polynucleotide strand;

(b) identifying the blocked, labeled nucleotide incorporated into the copy polynucleotide strand;

(c) removing a label and a blocking moiety from the blocked, labeled nucleotide incorporated into the copy polynucleotide strand;

(d) washing the removed label and the blocking moiety away from the copy polynucleotide strand with a first wash composition comprising a second polymerase wherein the first wash composition is substantially free of Mg.sup.2+ to inhibit the second polymerase from incorporating a nucleotide into the copy polynucleotide strand; and (e) repeating steps (a) to (d) until at least a partial sequence of the template polynucleotide strand is determined.

2. The method of claim 1, wherein the first wash composition comprises a plurality of nucleotides.

3. The method of claim 2, wherein the plurality of nucleotides comprises blocked nucleotides.

4. The method of claim 2, wherein the plurality of nucleotides comprises nucleotides labeled with a detectable moiety.

5. The method of claim 1, wherein the template polynucleotide strand is immobilized on a solid support.

6. The method of claim 1, wherein the template polynucleotide is immobilized on a surface of a flow cell.

7. A polynucleotide sequencing method comprising:

(a) incubating an incorporation composition comprising a first polymerase and a plurality of blocked, labeled nucleotides with a template polynucleotide strand such that the first polymerase incorporates one of the plurality of blocked, labeled nucleotides into a copy polynucleotide strand complementary to at least a portion of the template polynucleotide strand;

(b) identifying the blocked, labeled nucleotide incorporated into the copy polynucleotide strand;

(c) contacting the copy polynucleotide strand into which the blocked, labeled nucleotide is incorporated with a first wash composition comprising a second polymerase wherein the first wash composition is substantially free of Mg.sup.2+ to inhibit the second polymerase from incorporating a nucleotide into the copy polynucleotide strand;

(d) removing a label and a blocking moiety from the blocked, labeled nucleotide incorporated into the copy polynucleotide strand;

(e) washing the removed label and the blocking moiety away from the copy polynucleotide strand with a second wash composition; and (f) repeating steps (a) to (e) until at least a partial sequence of the template polynucleotide strand is determined.

8. The method of claim 7, wherein the first wash composition comprises a plurality of nucleotides.

9. The method of claim 8, wherein the plurality of nucleotides comprises blocked nucleotides.

10. The method of claim 8, wherein the plurality of nucleotides comprises nucleotides labeled with a detectable moiety.

11. The method of claim 7, wherein the template polynucleotide strand is immobilized on a solid support.

12. The method of claim 7, wherein the template polynucleotide is immobilized on a surface of a flow cell.

* * * * *